US007335511B2

(12) United States Patent
Mountford et al.

(10) Patent No.: US 7,335,511 B2
(45) Date of Patent: *Feb. 26, 2008

(54) MAGNETIC RESONANCE SPECTROSCOPY TO CLASSIFY TISSUE

(75) Inventors: Carolyn E. Mountford, East Ryde (AU); Peter Russell, Pyme (AU); Ian C. P. Smith, Winnipeg (CA); Rajmund L. Somorjai, Headingly (CA)

(73) Assignees: University of Sydney, Sydney (AU); National Research Council of Canada, Ontario (CA)

( * ) Notice: Subject to any disclaimer, the term of this patent is extended or adjusted under 35 U.S.C. 154(b) by 408 days.

This patent is subject to a terminal disclaimer.

(21) Appl. No.: 11/012,959

(22) Filed: Dec. 15, 2004

(65) Prior Publication Data

US 2005/0107683 A1 May 19, 2005

Related U.S. Application Data

(63) Continuation of application No. 09/691,776, filed on Oct. 18, 2000, now Pat. No. 6,835,572.

(60) Provisional application No. 60/160,029, filed on Oct. 18, 1999.

(51) Int. Cl.
*G01N 33/48* (2006.01)
*G06F 19/00* (2006.01)
*A61B 5/05* (2006.01)

(52) U.S. Cl. .................... 436/63; 436/173; 600/410; 702/19

(58) Field of Classification Search .................. 436/63, 436/173; 600/410, 416; 702/19
See application file for complete search history.

(56) References Cited

U.S. PATENT DOCUMENTS 6,835,572 B1 * 12/2004 Mountford et al. ........... 436/63

* cited by examiner

*Primary Examiner*—Arlen Soderquist
(74) *Attorney, Agent, or Firm*—Peter J. Phillips; Cooper & Dunham LLP

(57) ABSTRACT

Robust classification methods analyze magnetic resonance spectroscopy (MRS) data (spectra) of fine needle aspirates taken from breast tumors. The resultant data when compared with the histopathology and clinical criteria provide computerized classification-based diagnosis and prognosis with a very high degree of accuracy and reliability. Diagnostic correlation performed between the spectra and standard synoptic pathology findings contain detail regarding the pathology (malignant versus benign), vascular invasion by the primary cancer and lymph node involvement of the excised axillary lymph nodes. The classification strategy consisted of three stages: pre-processing of MR magnitude spectra to identify optimal spectral regions, cross-validated Linear Discriminant Analysis, and classification aggregation via Computerised Consensus Diagnosis. Malignant tissue was distinguished from benign lesions with an overall accuracy of 93%. From the same spectrum, lymph node involvement was predicted with an accuracy of 95% and tumor vascularisation with an overall accuracy of 92%.

8 Claims, 3 Drawing Sheets

MR Spectra with SNR >10. (A) Malignant, (B) Benign
For acquisition parameters see Materials and Methods.
A line broadening of 3Hz was applied to both spectra.
The spectra were displayed in absolute intensity mode
(noiselevel similar in both spectra).

MAGNETIC RESONANCE SPECTROSCOPY TO CLASSIFY TISSUE

CROSS REFERENCE TO RELATED APPLICATIONS

This application claims priority on, and incorporates by reference, U.S. Provisional Application Ser. No. 60/160,029 filed Oct. 18, 1999, now abandoned, and this application is a continuation of U.S. patent application Ser. No. 09/691, 776 filed Oct. 18, 2000, now U.S. Pat. No. 6,835,572.

STATEMENT REGARDING FEDERALLY SPONSORED RESEARCH DEVELOPMENT

The work described herein was supported by U.S. Army Grant number DAMD 17-96-1-6077 and NH & MRC 950215 and NH & MRC 973769.

BACKGROUND OF THE INVENTION

1. Technical Field of the Invention

The present invention relates to the use of magnetic resonance spectroscopy, and more particularly to such use for determining pathology, vascularization and nodel involvement of a biopsy of breast tissue.

2. Description of the Related Art

Within this application several publications are referenced by arabic numerals within parentheses. Full citations for these and other references may be found at the end of the specification immediately preceding the claims. The disclosures of all of these publications in their entireties are hereby incorporated by reference into this application in order to more fully describe the state of the art to which this invention pertains. Clinical evaluation, mammography and aspiration cytology or core biopsy (triple assessment) is undertaken on women presenting with breast lesions in most Western countries. Clinical assessment of palpable breast lumps is unreliable (1, 2). Impalpable lesions are usually discovered by screening or diagnostic mammography, which has a reported sensitivity of 77-94% and a specificity of 92-95% (3). Cytological assessment of fine needle aspiration biopsies (FNAB) has sensitivities ranging from 65-98% and specificities ranging from 34-100% (4) depending on the skill of the person performing the aspiration and the expertise of the cytopathologist.

Following surgical excision of the lesion a time consuming process of preparation and pathological assessment of the specimen determines the nature of the tumor and the prognostic features associated with it.

SUMMARY OF THE INVENTION

Magnetic resonance spectroscopy (MRS) is a modality with a proven record in the diagnosis of minimally invasive malignant lesions (5-11). MR spectra of small samples of tissue or even cell suspensions enable the reliable determination of whether the tissue of origin is malignant or benign. Often MRS is able to detect malignancy before morphological manifestations are visible by light microscopy (8).

The potential of proton MRS from FNAB specimens to distinguish benign from malignant breast lesions has been demonstrated previously (12). At that time the MRS method relied on visual reading to process spectra and calculate the ratio of the diagnostic metabolites choline and creatine. This spectral ratio allowed tissue to be identified as either benign or malignant. In a small cohort of 20 patients within that study it also distinguished high grade ductal carcinoma in situ (DCIS) with comedonecrosis or microinvasion from low grade DCIS. Despite the limitation of visual inspection, which could only assess those spectra with a signal to noise ratio (SNR) of greater than 10, the visual method resulted in a diagnosis of malignant or benign with a sensitivity and specificity of 95 and 96%. FIG. 1 shows malignant and benign spectra with good SNR while FIG. 2 shows spectra with poor SNR.

Twenty percent of the spectra were discarded because low aspirate cellularity yielded inadequate SNR. In the initial study visual analysis used only two of fifty or more available resonances (6). Thus, potentially diagnostic and prognostic information in the remaining spectrum may have been ignored.

A 3-stage, robust statistical classification strategy (SCS) has been developed to classify biomedical data and to assess the full MR spectrum obtained from biological samples. The robustness of the method has been demonstrated previously with the analysis of proton MR spectra of thyroid tumors (13), ovarian (14), prostate (9), and brain tissues (15). The present invention applies SCS to assess proton MR spectra of breast aspirates against pathological criteria in order to determine the correct pathology on samples with sub-optimal cellularity and SNR and to determine if other diagnostic and prognostic information is available in the spectra.

The inventors have determined that SCS on MRS from breast FNAB is more reliable than visual inspection to determine whether a lesion is benign or malignant, and that a greater proportion of spectra is useful for analysis. Furthermore, spectral information obtained from MRS on FNAB of breast cancer specimens predicted lymph node metastases (overall accuracy of 96%) and vascular invasion (overall accuracy of 92%).

The invention provides a method for obtaining a statistical classifier for classifying spectral data from a biopsy of breast tissue to determine the classification of a characteristic of the breast tissue, comprising:

(a) locating a plurality of maximally discriminatory subregions in magnetic resonance spectra of biopsies of breast tissue having known classifiers of a characteristic, (b) cross-validating the spectra by selecting a portion of the spectra, developing linear discriminant analysis classifiers from said first portion of spectra, and validating the remainder of the spectra using the classifiers from the first portion of the spectra, to obtain optimized linear discriminant analysis coefficients, (c) repeating step (b) a plurality of times, each time selecting a different portion of the spectra, to obtain a different set of optimized linear discriminant analysis coefficients for each of said plurality of times;

(d) obtaining a weighted average of the linear discriminant analysis coefficients to obtain final classifier spectra indicating the classification of the characteristic based on the spectra; and (e) comparing spectra from a biopsy of breast tissue of unknown classification of a characteristic to the final classifier spectra to determine the classification of the characteristic of the breast tissue.

The invention provides an apparatus for obtaining a statistical classifier for classifying spectral data from a biopsy of breast tissue to determine the classification of a characteristic of the breast tissue, comprising:

(a) a locator for locating a plurality of maximally discriminatory subregions in magnetic resonance spectra of biopsies of breast tissue having known classifiers of a characteristic of breast tissue, (b) a cross-validator for selecting a portion of the spectra, developing linear discriminant analysis classifiers from said first portion of spectra, and validating the remainder of the spectra using the classifiers from the first portion of the spectra, to obtain optimized linear discriminant analysis coefficients, said cross-validator selecting, developing and validating a plurality of times, each time selecting a different portion of the spectra, to obtain a different set of optimized linear discriminant analysis coefficients for each of said plurality of times, and (c) an averager for obtaining a weighted average of the linear discriminant analysis coefficients to obtain final classifier spectra indicating the classification of the characteristic based on the spectra, whereby spectra from a biopsy of breast tissue of unknown classification of a characteristic may be compared to the final classifier spectra to determine the classification of the characteristic of the breast tissue.

The invention provides a method for determining the classification of a characteristic of breast tissue, comprising:
obtaining magnetic resonance spectra of a biopsy of breast tissue having unknown classification of a characteristic and comparing the spectra with a classifier, said classifier having been obtained by:

(a) locating a plurality of maximally discriminatory sub-regions in the magnetic resonance spectra of biopsies of breast tissue having known classifications of a characteristic of the breast tissue, (b) cross-validating the spectra of (a) by selecting a portion of spectra, developing linear discriminant analysis classifier from said first portion of spectra, and validating the remainder of the spectra using the classifications from the first portion of the spectra, to obtain optimized linear discriminant analysis coefficients, (c) repeating step (b) a plurality of times, each time selecting a different portion of the spectra, to obtain a different set of optimized linear discriminant analysis coefficients for each of said plurality of times, and (d) obtaining a weighted average of the linear discriminant analysis coefficients to obtain final classifier spectra indicating the classification of the characteristic based on the spectra, and comparing the spectra from the biopsy of breast tissue having unknown classification to the final classifier spectra to determine the classification of the characteristic of the breast tissue.

The invention provides an apparatus for determining the classification of a characteristic of breast tissue, comprising:
a spectrometer for obtaining magnetic resonance spectra of a biopsy of breast tissue having unknown classification of a characteristic;
a classifier for statistically classifying the spectra by comparing the spectra with a reference classifications, said classifier having been obtained by:

(a) locating a plurality of maximally discriminatory sub-regions in the magnetic resonance spectra of biopsies of breast tissue having known classifications of a characteristic of the breast tissue, (b) cross-validating the spectra of (a) by selecting a portion of spectra, developing linear discriminant analysis classifier from said first portion of spectra, and validating the remainder of the spectra using the classifiers from the first portion of the spectra, to obtain optimized linear discriminant analysis coefficients, (c) repeating step (b) a plurality of times, each time selecting a different portion of the spectra, to obtain a different set of optimized linear discriminant analysis coefficients for each of said plurality of times, and (d) obtaining a weighted average of the linear discriminant analysis coefficients to obtain final classifier spectra indicating the classification of the characteristic based on the spectra, and wherein said classifier compares the spectra from the biopsy of breast tissue having unknown classification to the final classifier spectra to determine the classification of the characteristic of the breast tissue.

DETAILED DESCRIPTION OF THE INVENTION

Methods

Figure 1:
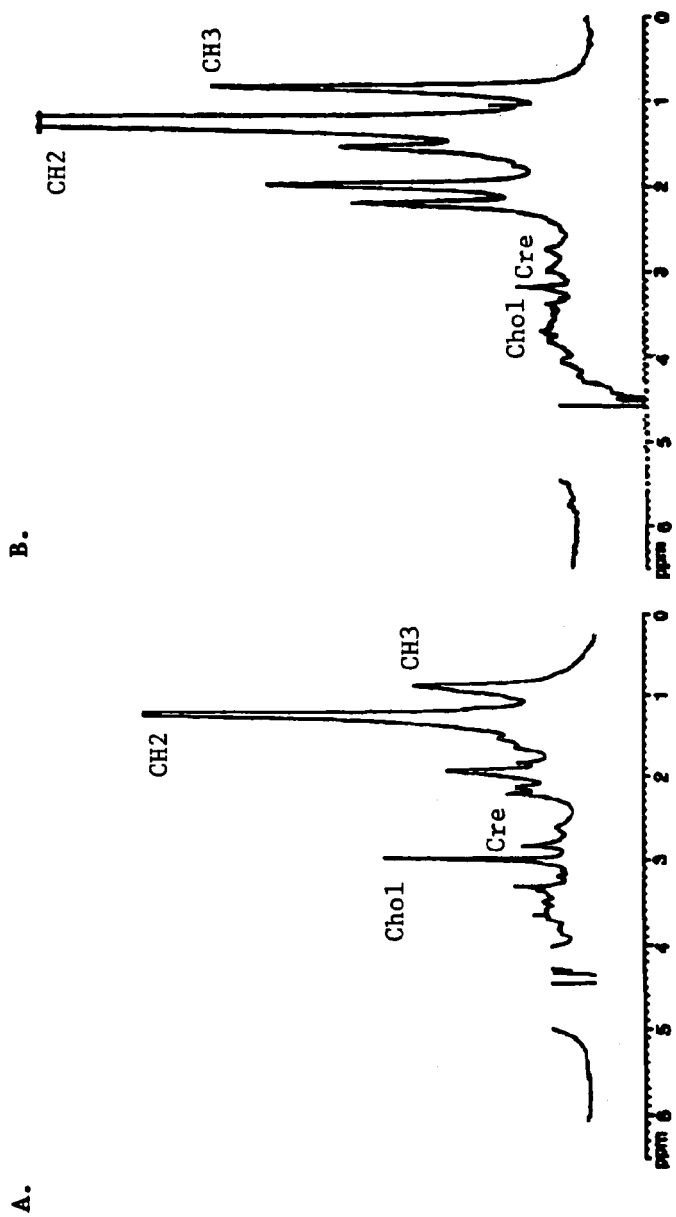
FIG. 1 shows malignant and benign spectra with relatively good SNR.
Figure 2:
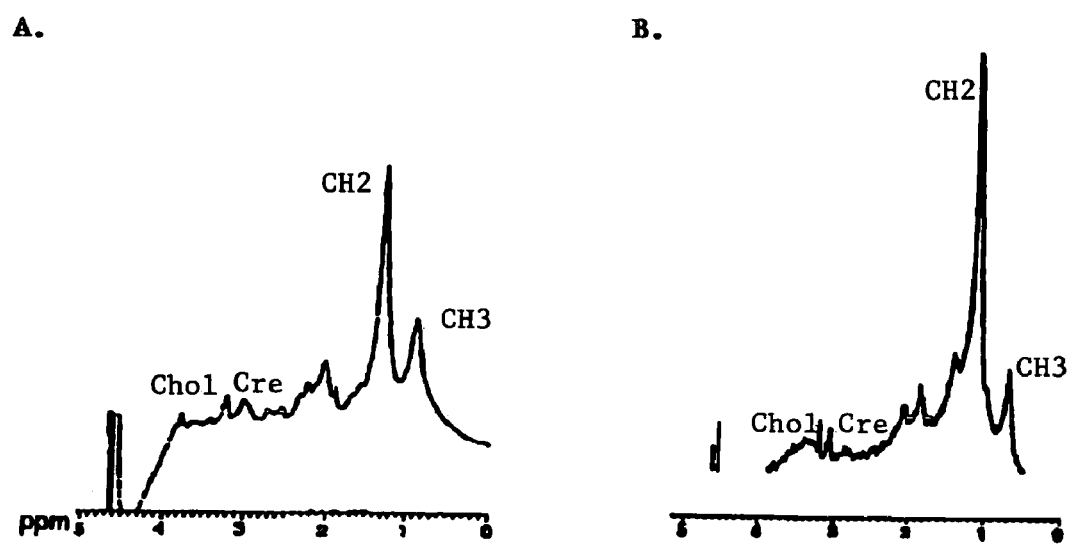
FIG. 2 shows spectra with relatively poor SNR.

Preparation of Patients:

Intra-operative FNAB were taken from 139 patients undergoing breast surgery for malignant and benign conditions (Table 1) by three surgeons in separate hospitals. In order to provide a sufficiently large data set for SCS an additional 27 patients joined the study (see Table 1). Impalpable breast lesions that had been localised by carbon track or hook wire were included except if the lesion was not palpable at excision or when the pathology specimen could have been compromised. All samples were taken during surgery under direct vision after the lesion had been identified and incised sufficiently widely to ensure that the FNAB and tissue specimens represented the same lesion and were thus comparable. The lesion was identified and incised in-vivo via the margin with the greatest apparent depth of normal tissue between it and the lesion to ensure the pathologist could report upon the lesion according to a standard protocol. Malignant and suspicious lesions were orientated with sutures and radio opaque vascular clips (Ligaclips) for pathological and radiological orientation. The FNAB was collected by the surgeon using a 23-gauge needle on a 5 ml syringe. The number of needle passes was recorded and the surgeon's evaluation of the quality of the aspirate was made. Before the needle was removed from the lesion, a tissue sample including the relevant part of the needle track was taken. The size of this tissue specimen was estimated and recorded by the surgeon.

Pre-operative clinical and investigative data included localised pain, nipple discharge or nipple crusting, details of previous mammography, and whether the lesion was detected through screening. The clinical, mammography, ultra sonographic, cytological, core biopsy and MRI details were recorded as malignant, suspicious, benign, impalpable, uncertain or not done.

The pathology specimen was sent on ice at the initial stages, but later in formalin, for standard histopathological reporting and hormone receptor analysis. The pathology report was issued in synoptic format (16).

Specific tumor-related clinical and sampling information was collected. These included a history of previous breast biopsies with dates, diagnoses, sizes and sites of these lesions along with the current lesion's duration, palpability, laterality, size and locality within the breast. The date of operation, the extent of breast surgery from open biopsy to total mastectomy, and axillary surgery from sampling to level 3 dissection was recorded.

Specimen Preparation:

Following complete excision of the lesions the FNAB cytology and tissue specimens were placed in polypropylene vials containing 300 ml phosphate-buffered saline (PBS) in $D_2O$. All specimens were immediately immersed in liquid nitrogen and stored at −70° C. for up to 6 weeks until MRS analysis.

Prior to the proton MRS experiment, each FNAB specimen was thawed and transferred directly to a 5 mm MRS tube. The volume was adjusted to 300 ml with $PBS/D_2O$ where necessary. Proton MRS assessment of all specimens was performed without knowledge of the correlative histopathology, either from the synoptic pathology report or from sectioning of tissue used in MRS study.

The sample of tissue excised around the needle tract was similarly placed in polypropylene vials containing 300 ml $PBS/D_2O$ and immersed in liquid nitrogen as described above. This sample was later used for pathological correlation.

Data Acquisition:

MRS experiments were carried out on a Bruker Avance 360 wide-bore spectrometer (operating at 8.5 Tesla) equipped with a standard 5 mm dedicated proton probehead. The sample was spun at 20 Hz and the temperature maintained at 37° C. The residual water signal was suppressed by selective gated irradiation. The chemical shifts of resonances were referenced to aqueous sodium 3-(trimethylsilyl)-propanesulphonate (TSPS) at 0.00 ppm. One-dimensional spectra were acquired over a spectral width of 3597 Hz (10.0 ppm) using a 90° pulse of 6.5-7 μs, 8192 data points, 256 accumulations and a relaxation delay of 2.00 seconds, resulting in a pulse repetition time of 3.14 seconds.

SNR was determined using the Bruker standard software (xwinnmr). The noise region was defined between 8.5 to 9.5 ppm. The signal region was defined between 2.8 to 3.5 ppm.

Histopathology:

Diagnostic correlation was obtained by comparing spectral analysis with the hospital pathology report provided for each patient. Lymph node involvement and vascular invasion were determined from the reports only in cases where this information was complete. In the participating hospitals lymph nodes were embedded and serial sectioned in standard fashion. One 5 μm section out of every 50 (i.e., each 250 μm) was stained and examined. All intervening sections were discarded.

In the initial phase of the study, cytological analysis of the aspirate after MRS analysis was attempted but cellular detail was compromised by autolytic changes and this approach was not pursued. In order to verify FNAB sampling accuracy, a separate histopathological assessment by a single pathologist (PR) was obtained from tissue removed from the aspiration site of the MRS sample. Tissue specimens were thawed, fixed in FAA (formalin/acetic acid/alcohol), paraffin-embedded, sectioned at 7 μm, stained with haematoxylin and eosin according to standard protocols and reviewed under the light microscope by the pathologist without access to the clinical or MRS data. Tissue preservation, abundance of epithelial cells relative to stroma, and resence of potentially confounding factors such as fat and inflammatory cells were reported in addition to the principal diagnosis.

Statistical Classification Strategy:

The general classification strategy has been developed and was designed specifically for MR and IR spectra of biofluids and biopsies. The strategy consists of three stages. First the MR magnitude spectra are preprocessed, (in order to eliminate redundant information and/or noise) by submitting them to a powerful genetic algorithm-based Optimal Region Selection (ORS_GA) (17), which finds a few (at most 5-10) maximally discriminatory subregions in the spectra. The spectral averages in these subregions are the ultimate features and used at the second stage. This stage uses the features found by ORS_GA to develop Linear Discriminant Analysis (LDA) classifiers that are made robust by IBD's bootstrap-based crossvalidation method (18). The crossvalidation approach proceeds by randomly selecting about half the spectra from each class and using these to train a classifier (usually LDA). The resulting classifier is then used to validate the remaining half. This process is repeated B times (with random replacement), and the optimized LDA coefficients are saved. The weighted average of these B sets of coefficients produces the final classifier. The ultimate classifier is the weighted output of the 500-1000 different bootstrap classifier coefficient sets and was designed to be used in a clinical setting as the single best classifier. The classifier consists of probabilities of class assignment for the individual spectra. For 2-class problems, class assignment is called crisp if the class probability is >0.75%. For particularly difficult classification problems the third stage is activated. This aggregates the outputs (class probabilities) of several independent classifiers to form a Computerised Consensus Diagnosis (CCD) (13, 15). The consequence of CCD is that classification accuracy and reliability is generally better than the best of the individual classifiers.

Figure 3:
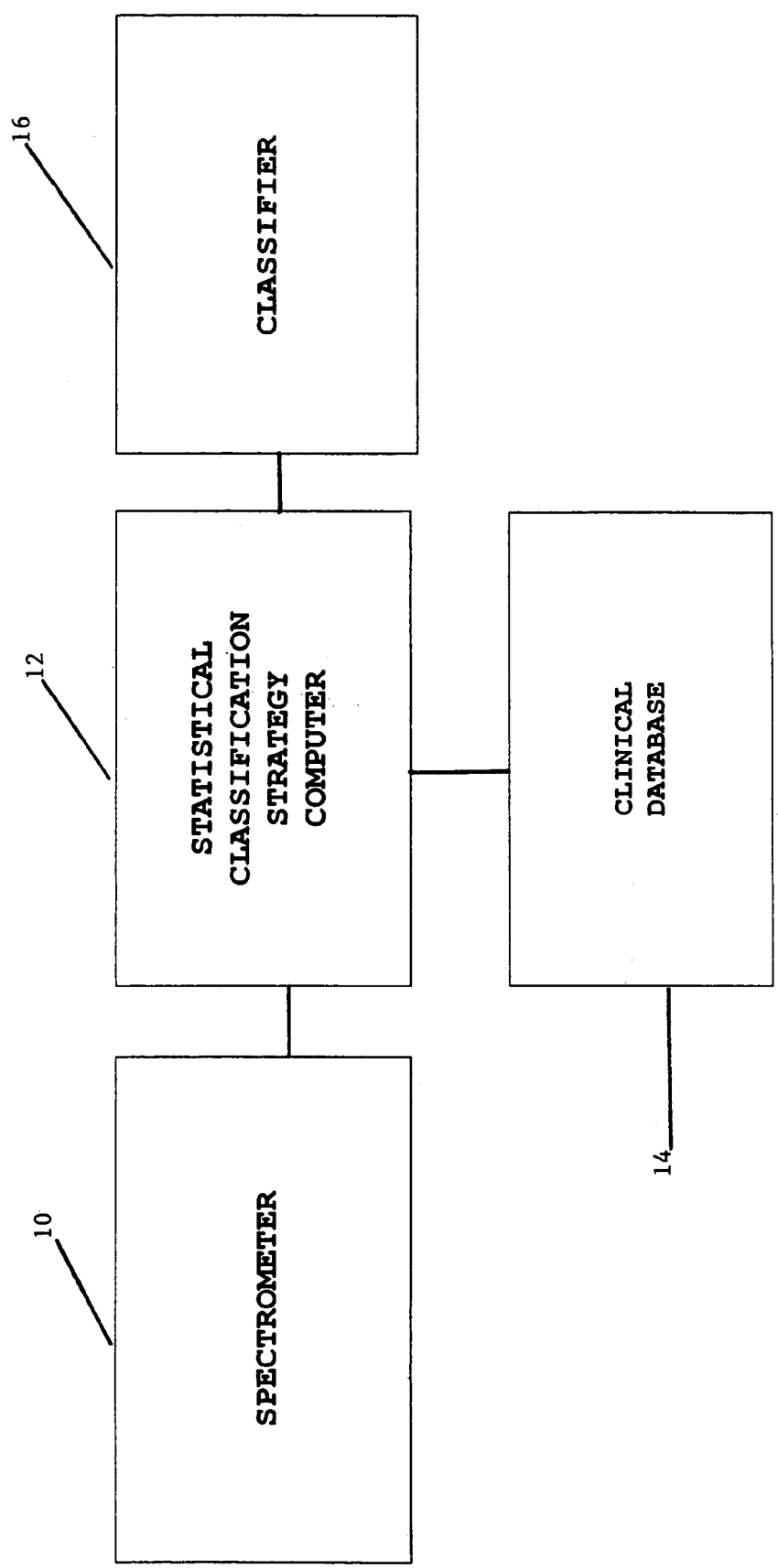
FIG. 3 shows a system for determining pathology, vascularization and nodal involvement according to the invention.

FIG. 3 shows a spectrometer 10, which may be a Bruker Avance 360 spectrometer operating at 8.5 Tesla, with equipped computer. The statistical classification strategy (SCS) computer 12 stores the SCS and other programs described herein. The clinical data base includes the information from the data acquisition and histopathology, used by the computer 12 to develop the classifier 16. The classifier 16 classifies the characteristics (e.g. pathology, vascularization and/or lymph node involvement) of the breast tissue under examination.

Results

One hundred and sixty-six patients were involved in the study. A summary of the clinicopathological criteria is shown in Table 1.

Benign Versus Malignant:

Proton MR spectra were recorded for each FNAB irrespective of the cellularity of the aspirate. However, those specimens with a SNR less than 10, which were shown to be inadequate for visual inspection (12) have been included in the SCS analysis without significantly compromising accuracy. Visual inspection of all spectra irrespective of signal to noise gave a sensitivity and specificity of 85.3% and 81.5% respectively (Table 2a), based on the creatine-to-choline ratio. When SCS-based classifiers were developed for all available spectra (Table 2b), 96% of the spectra were considered crisp and could be assigned unambiguously by the classifier as malignant or benign. Sensitivity and specificity were 93% and 92% respectively.

After removing the 31 spectra with the previously determined poor SNR (SNR<10), a sensitivity and specificity of 98% and 94%, respectively, was achieved with crispness of 99% (Table 2c).

Prognostic factors:

With the addition of prognostic criteria to the database two further classifiers were created, namely, lymph node involvement and vascular invasion. A small number of known benign or pre-invasive cases were included in these subsets to assess the computer's ability to correctly define those cases in which no nodal involvement or vascular invasion was expected. These benign or pre-invasive cases were all correctly assigned by the computer into their respective uninvolved classes.

Lymph Node Involvement:

There were 31 cases with nodal involvement and 30 without including 2 DCIS and 3 fibrocystic specimens. All spectra were included irrespective of SNR. Only those spectra for which complete pathology and clinical reports were available were included in this comparison (Table 1). The presence of lymph node metastases was predicted by SCS with a sensitivity of 96% and specificity of 94% (Table 3a).

Vascular Invasion:

SCS-based analysis of spectra was also carried out using vascular invasion as the criterion. There were 85 spectra for this analysis (Table 1). A sensitivity of 84% and specificity of 100% was achieved for the correct determination of vascular invasion, with an overall accuracy of 92% (Table 3b).

Discussion

The introduction of preprocessing and SCS analysis of MR spectra has enhanced the ability to correlate spectroscopic changes with the pathology of human biopsies. It has also allowed specimens with sub-optimal cellularity to be analysed, and more importantly, provided a correlation with clinical criteria not apparent by visual inspection.

Visual inspection of spectra, like histopathology, is limited by the experience and skill of the reader for determining peak height ratios of metabolites (12). Visual inspection of spectra and the use of peak height ratio measurements of choline and creatine discriminated benign from malignant spectra with a higher degree of accuracy than standard triple assessment of breast lesions. However, to attain a high degree of accuracy, many spectra with poor SNR had to be discarded, reducing the effectiveness of the technique. Previous estimates of cellular material derived from FNAB, on which to perform MRS analysis reliably, have suggested that at least $10_6$ cells are needed (6).

By using SCS-derived classifiers it was possible to distinguish malignant from benign pathologies with higher sensitivity 92% and specificity 96% for all FNAB spectra including those with low SNR (Table 2b) than by visual reading of these same spectra (Table 2a). That SCS-based analysis could more reliably classify a greater proportion of spectra than could be visually assessed is testament to the robustness and greater generality of the computer-based approach.

The SCS-based result is further improved by presenting to the computer spectral data with high SNR. The improvement in sensitivity and specificity gained for spectra with SNR>10 (Table 2c) illustrates this point. Obtaining FNAB with adequate cell numbers can also enhance the results.

SCS permits classifiers to recognise patterns containing more complex information. The classifier has been validated to diagnose specimens with lymph node involvement and vascular invasion. The ability of the SCS-derived classifier to predict lymph node involvement with an accuracy of 95% and vascular invasion with an accuracy of 92% emphasises the wealth of chemical information that can be extracted, with the appropriate statistical approach, from an FNAB of a breast lesion (Table 3).

A major challenge in breast cancer is the need to identify and understand the factors that most influence the patient's prognosis and through timely and appropriate intervention influence this outcome. Adjuvant therapy can reduce the odds of death during the first ten years after diagnosis of breast cancer by about of 20-30% (19). The best prognostic indicator of survival in patients with early breast cancer has been shown to be axillary lymph node status (20-22).

Increasingly, sentinel lymph node biopsy is being investigated as a means to reduce the morbidity and cost of unnecessary axillary dissection in the two thirds of women with early invasive breast cancer who prove to be node-negative (23-25), while preserving the option of full axillary node clearance in those patients who are node-positive. MRS may possibly determine nodal involvement from the cellular material derived solely from the primary tumor, thus limiting the role of sentinel lymph node biopsy.

The results, that 52% of patients with lymph node involvement also had vascular invasion, is in agreement with Barth et al (26), who showed that peritumoural lymphovascular invasion correlated with lymph node involvement (27) and was an independent predictor of disease free and overall survival (28-31).

A computer-based statistical classification strategy providing a robust means of analysing clinical data is becoming a reality. The power, speed and reproducibility of a computer-based diagnosis may lead to suitably programmed computers supplanting the human observer in the clinical laboratory. Patients increasingly expect certainty in diagnosis and optimum management.

Several important experimental factors should be noted. Presently, the MRS method according to the invention has thus far been demonstrated to work only on aspirated cells from the breast and not on core biopsies that contain a sufficiently high level of fat to mask diagnostic and prognostic information. The biopsy should be representative of the lesion and contain sufficient cellularity. Furthermore, sample handling is of paramount importance if the specimen is to be minimally degraded. Quality control in the spectrometer should be exercised with regard to pulse sequences, temperature, magnet stability, shimming and water suppression. The magnetic field at which the database reported herein was collected is 8.5 Tesla (360 MHz for proton).

Because spectral patterns are frequency dependent, a new classifier should be developed if one uses different magnetic field strengths.

The clinical and pathology databases used to train the classifier should be representative of the full range of pathologies or the complete demographics of the population, or else the classifier may be inadequately prepared for all the possibilities it might encounter in clinical practice. In developing a database for breast lesions, the training set should have adequate samples of all the commonly encountered breast pathologies and be updated upon detection of less common tumour types.

The invention is expected to provide a revolutionary impact on breast cancer management by the use of SCS computerised analysis of MR spectral features, by obtaining a much higher level of accuracy in diagnosis of the lesion and also an indication of its metastatic potential when compared to visual inspection of spectra. Most importantly, the invention facilitates identification of the stage of the disease from spectral information of FNAB collected only from the primary breast lesion.

The invention allows one to determine pathological diagnosis, the likelihood of axillary lymph nodal involvement and tumor vascularisation by SCS-based analysis of proton MR spectra of a FNAB taken from a primary breast lesion. The SCS-based method is more accurate and reliable than visual inspection for identifying complex spectral indicators of diagnosis and prognosis.

The ability of an SCS-based analysis of MRS data to provide prognostic information on lymph node involvement by sampling only the primary tumor may provide a paradigm shift in the management of breast cancer. The determination of vascular invasion from the same cellular material highlights the untapped potential of MRS to determine prognostic information.

Although one embodiment of the invention has been shown and described, numerous variations and modifications will readily occur to those skilled in the art. The invention is not limited to the preferred embodiment, and its scope is determined only by the appended claims.

TABLE 2

Maglignant versus Benign a. Visual Inspection: Malignant versus Benign

|  | Sensitivity | Specificity |
|---|---|---|
| For all Spectra |  |  |
| Malignant (n = 83) vs Benign (n = 57) | 85.3% | 81.5% |
| Spectra SNR > 10 |  |  |
| Malignant (n = 60) vs Benign (n = 49) | 100% | 87.3% | b. SCS: Malignant or Benign (All spectra): (M: 83, B: 57)

|  | B | M | Sensitivity | Specificity | PPV | % Crisp |
|---|---|---|---|---|---|---|
| B | 51 | 4 | 92.7% | 92.4% | 92.4% | 96.5% |
| M | 6 | 73 | 92.4% | 92.7% | 92.7% | 95.2% |

Overall Accuracy: 92.6%
Overall % Crisp: 95.7% (134 of 140)
$x = 0.922$ c. SCS: Malignant or Benign (SNR > 10): (M: 60, B: 49)

|  | B | M | Sensitivity | Specificity | PPV | % Crisp |
|---|---|---|---|---|---|---|
| B | 46 | 3 | 93.9% | 98.3% | 98.2% | 100.0% |
| M | 1 | 58 | 98.3% | 93.9% | 94.1% | 98.3% |

Overall Accuracy: 96.1%
Overall % crisp: 99.1% (108 of 109)
$x = 0.922$

TABLE 3

SCS:-Prognostic Indicators a. Lymph Node involvement: (P: (Present) 29, A: (Absent) 32)

|  | P | A | Sensitivity | Specificity | PPV | % Crisp |
|---|---|---|---|---|---|---|
| P | 25 | 1 | 96.2% | 93.8% | 93.9% | 89.7% |
| A | 2 | 30 | 93.8% | 96.2% | 96.1% | 100% |

Overall Accuracy: 95.0%
Overall % crisp: 95.1% (58 of 61)
$x = 0.899$

TABLE 1

Summary of Clinico-pathological Data

|  | All patients (n = 66) | Benign/Malignant (n = 140) | Lymph Nodes (n = 61) | Vascular Invasion (n = 85) |
|---|---|---|---|---|
|  | Age Mean ± SD (Range) | | | |
| Pathology type | 55.8 ± 15.4 (20-101) | 54.7 ± 15 (20-90) | 58.4 ± 13.2 (29-85) | 60.6 ± 14.3 (29-101) |
| Invasive Ductal | 89 | 74 | 52 | 68 |
| Invasive Lobular | 8 | 8 | 3 | 5 |
| Mixed Ductal/Lob. | 1 | 1 | 1 |  |
| DCIS | 10 | 1 | 2* | 9* |
| Fibroadenoma | 17 | 17 |  |  |
| Fibrocystic | 22 | 22 | 3* | 2* |
| Papilloma | 3 | 2 |  |  |
| Radial Scar | 2 | 2 |  |  |
| Gynaecomastia | 1 | 1 |  |  |
| Misc. Benign | 13 | 12 |  | 1 |
| Total | 166 | 140 | 61 | 85 |

*These preinvasive and benign lesions were included as known lymph node negative, vascular invasion negative cases to test the computer's ability to discern true negatives and positives. They were all correctly classified by the computer into their respective classes.

TABLE 3-continued

SCS:-Prognostic Indicators b. Vascular Invasion: (P: (Present) 33, A: (Absent) 52)

|   | P | A | Sensitivity | Specificity | PPV | % Crisp |
|---|---|---|---|---|---|---|
| P | 26 | 5 | 83.9% | 100.0% | 100.0% | 93.9% |
| A | 0 | 49 | 100.0% | 83.9% | 86.1% | 94.2% |

Overall Accuracy: 91.9%
Overall % crisp: 94.1% (80 of 85)
x = 0.839

REFERENCES

1. Kitchen P R, McLennan R, Mursell A. Node-positive breast cancer: a comparison of clinical and pathological findings and assessment of axillary clearance. Australian & New Zealand Journal of Surgery 1980; 50:580-3.
2. Dixon J M, Senbanjo R O, Anderson T J, mammography. Risk of breast cancer based on age and mammographic interpretation [JAMA 1996; 276:39-43].
4. Giard R W, Hermans J. The value of aspiration cytologic examination of the breast. A statistical review of the medical literature. Cancer 1992; 69:2104-10.
5. Delikatny E J, Russell P, Hunter J C, et al. Proton MR and human cervical neoplasia: ex-vivo spectroscopy allows distinction of invasive carcinoma of the cervix from carcinoma in-situ and other preinvasive lesions. Radiology 1993; 188:791-6.
6. Lean C L, Delbridge L, Russell P, et al. Diagnosis of follicular thyroid lesions by proton magnetic resonance on fine needle biopsy. Journal of Clinical Endocrinology & Metabolism 1995; 80:1306-11.
7. Lean C L, Newland R C, Ende D A, Bokey E L, Smith I C, Mountford C E. Assessment of human colorectal biopsies by 1H MRS: correlation with histopathology. Magnetic Resonance in Medicine 1993; 30:525-33.
8. Russell P, Lean C L, Delbridge L, May G L, Dowd S, Mountford C E. Proton magnetic resonance and human thyroid neoplasia. I: Discrimination between benign and malignant neoplasms. American Journal of Medicine 1994; 96:383-8.
9. Hahn P, Smith I C, Leboldus L, Littman C, Somorjai R L, Bezabeh T. The classification of benign and malignant human prostate tissue by multivariate analysis of 1H magnetic resonance spectra. Cancer Research 1997; 57:3398-401.
10. Rutter A, Hugenholtz H, Saunders J K, Smith I C. Classification of brain tumors by ex vivo 1H NMR spectroscopy. Journal of Neurochemistry 1995; 64:1655-61.
11. Mountford C E, Lean C L, Hancock R, et al. Magnetic resonance spectroscopy detects cancer in draining lymph nodes. Invasion & Metastasis 1993; 13:57-71.
12. Mackinnon W B, Barry P A, Malycha P L, et al. Fine-needle biopsy specimens of benign breast lesions distinguished from invasive cancer ex vivo with proton MR spectroscopy. Radiology 1997; 204:661-6.
13. Somorjai R L, Nikulin A E, Pizzi N, et al. Computerized consensus diagnosis: a classification strategy for the robust analysis of MR spectra. I. Application to 1H spectra of thyroid neoplasms. Magnetic Resonance in Medicine 1995; 33:257-63.
14. Wallace J C, Raaphorst G P, Somorjai R L, et al. Classification of 1H MR spectra of biopsies from untreated and recurrent ovarian cancer using linear discriminant analysis. Magnetic Resonance in Medicine 1997; 38:569-76.
15. Somorijai R L, Dolenko B, Nikulin A K, et al. Classification of 1H MR spectra of human brain neoplasms: the influence of preprocessing and computerized consensus diagnosis on classification accuracy. Journal of Magnetic Resonance Imaging 1996; 6:437-44.
16. The Pathology reporting of Breast Cancer, Recommendations of the Australian Cancer Network. May 1977, The Stone Press, Epping NSW.
17. Nikulin A E, Dolenko B, Bezabeh T, Somorijai R L. Near-optimal region selection for feature space reduction: novel preprocessing methods for classifying MR spectra. NMRBiomed 1998; 11:209-217.
18. Efron B, Tibshirani R J. An Introduction to the Bootstrap. Monograms of Statistics and Applied Probability. Vol. 57: Chapman Hill, New York, 1993.
19. Weidner N. Prognostic factors in breast carcinoma. Current Opinion in Obstetrics & Gynecology 1995; 7:4-9.
20. Fisher B, Ravdin R G, Ausman R K, Slack N H, Moore G E, Noer R J. Surgical adjuvant chemotherapy in cancer of the breast: results of a decade of cooperative investigation. Annals of Surgery 1968; 168:337-56.
21. Silverstein M J, Gierson E D, Waisman J R, Senofsky G M, Colbum W J, Gamagami P. Axillary lymph node dissection for T1a breast carcinoma. Is it indicated? Cancer 1994; 73:664-7.
22. Chen Y Y, Schriitt S J. Prognostic factors for patients with breast cancers 1 cm and smaller. Breast Cancer Research & Treatment 1998; 51:209-25.
23. Cady B. The need to reexamine axillary lymph node dissection in invasive breast cancer [editorial]. Cancer 1994; 73:505-8.
24. Beechey-Newman N. Sentinel node biopsy: a revolution in the surgical management of breast cancer? Cancer Treatment Reviews 1998; 24:185-203.
25. Hill A D, Mann G B, Borgen P I, Cody H S, 3rd. Sentinel lymphatic mapping in breast cancer. Journal of the American College of Surgeons 1999; 188:545-9.
26. Barth A, Craig P H, Silverstein M J. Predictors of axillary lymph node metastases in patients with T1 breast carcinoma [Cancer 1997; 79:1918-22.]
27. Chadha M, Chabon A B, Friedmann P, Vikram B. Predictors of axillary lymph node metastases in patients with T1 breast cancer. A multivariate analysis. Cancer 1994; 73:350-3.
28. Rosen P P, Groshen S, Saigo P E, Kinne D W, Hellman S. Pathological prognostic factors in stage I (T1N0M0) and stage II (T1N1M0) breast carcinoma: a study of 644 patients with median follow-up of 18 years. Journal of Clinical Oncology 1989; 7:1239-51.
29. Pinder S E, Ellis I O, Galea M, O'Rouke S, Blamey R W, Elston C W. Pathological prognostic factors in breast cancer. III. Vascular invasion: relationship with recurrence and survival in a large study with long-term follow-up. Histopathology 1994; 24:41-7.
30. De Laurentiis M, Gallo C, De Placido S, et al. A predictive index of axillary nodal involvement in operable breast cancer. British Journal of Cancer 1996; 73:1241-7.
31. Lauria R, Perrone F, Carlomagno C, et al. The prognostic value of lymphatic and blood vessel invasion in operable breast cancer. Cancer 1995; 76:1772-8.

We claim:

1. A method for obtaining a statistical classifier for classifying spectral data from a biopsy of tissue to determine the classification of a characteristic of the tissue, comprising:
   (a) locating a plurality of discriminatory subregions in magnetic resonance spectra of biopsies of tissue having known classifiers of a characteristic,
   (b) cross-validating the spectra by selecting a first portion of the spectra comprising about one-half of the spectra leaving the other one-half of the spectra in the remaining portion of the spectra, developing linear discriminant analysis classifiers from said first portion of spectra, and validating the remainder of the spectra using the classifiers from the first portion of the spectra, to obtain optimized linear discriminant analysis coefficients,
   (c) repeating step (b) a plurality of times, each time selecting a different portion of the spectra, to obtain a different set of optimized linear discriminant analysis coefficients for each of said plurality of times; and
   (d) obtaining an average of the linear discriminant analysis coefficients to obtain final classifier spectra indicating the classification of the characteristic based on the spectra, wherein spectra from a biopsy of tissue of unknown classification of a characteristic may be compared to the final classifier spectra to determine the classification of the characteristic of the tissue.

2. An apparatus for obtaining a statistical classifier for classifying spectral data from a biopsy of tissue to determine the classification of a characteristic of the tissue, comprising:
   (a) a locator for locating a plurality of discriminatory subregions in magnetic resonance spectra of biopsies of tissue having known classifiers of a characteristic of tissue,
   (b) a crossvalidator for selecting a first portion of the spectra comprising about one-half of the spectra leaving the other one-half of the spectra in the remaining portion of the spectra, developing linear discriminant analysis classifiers from said first portion of spectra, and validating the remainder of the spectra using the classifiers from the first portion of the spectra, to obtain optimized linear discriminant analysis coefficients, said cross-validator selecting, developing and validating a plurality of times, each time selecting a different portion of the spectra, to obtain a different set of optimized linear discriminant analysis coefficients for each of said plurality of times, and
   (c) an averager for obtaining an average of the linear discriminant analysis coefficients to obtain final classifier spectra indicating the classification of the characteristic based on the spectra,
   whereby spectra from a biopsy of tissue of unknown classification of a characteristic may be compared to the final classifier spectra to determine the classification of the characteristic of the tissue.

3. A method for determining the classification of a characteristic of tissue, comprising:
   obtaining magnetic resonance spectra of a biopsy of tissue having unknown classification of a characteristic and comparing the spectra with a classifier, said classifier having been obtained by:
   (a) locating a plurality of discriminatory subregions in the magnetic resonance spectra of biopsies of tissue having known classifications of a characteristic of the tissue,
   (b) cross-validating the spectra of (a) by selecting a first portion of spectra comprising about one-half of the spectra leaving the other one-half of the spectra in the remainder of the spectra, developing linear discriminant analysis classifier from said first portion of spectra, and validating the remainder of the spectra using the classifications from the first portion of the spectra, to obtain optimized linear discriminant analysis coefficients,
   (c) repeating step (b) a plurality of times, each time selecting a different portion of the spectra, to obtain a different set of optimized linear discriminant analysis coefficients for each of said plurality of times, and
   (d) obtaining a weighted average of the linear discriminant analysis coefficients to obtain final classifier spectra indicating the classification of the characteristic based on the spectra, wherein the spectra from the biopsy of tissue having unknown classification may be compared to the final classifier spectra to determine the classification of the characteristic of the tissue.

4. An apparatus for determining the classification of a characteristic of tissue, comprising:
   a spectrometer for obtaining magnetic resonance spectra of
   a biopsy of tissue having unknown classification of a characteristic;
   a classifier for statistically classifying the spectra by comparing the spectra with a reference classifications, said classifier having been obtained by:
   (a) locating a plurality of discriminatory subregions in the magnetic resonance spectra of biopsies of tissue having known classifications of a characteristic of the tissue,
   (b) cross-validating the spectra of (a) by selecting a first portion of spectra comprising about one-half of the spectra leaving the other one-half of the spectra in the remainder of the spectra, developing linear discriminant analysis classifier from said first portion of spectra, and validating the remainder of the spectra using the classifiers from the first portion of the spectra, to obtain optimized linear discriminant analysis coefficients,
   (c) repeating step (b) a plurality of times, each time selecting a different portion of the spectra, to obtain a different set of optimized linear discriminant analysis coefficients for each of said plurality of times, and
   (d) obtaining an average of the linear discriminant analysis coefficients to obtain final classifier spectra indicating the classification of the characteristic based on the spectra, and wherein said classifier compares the spectra from the biopsy of tissue having unknown classification to the final classifier spectra to determine the classification of the characteristic of the tissue.

5. A method for obtaining a statistical classifier for classifying spectral data from a biopsy of tissue to determine the classification of a characteristic of the tissue, comprising:
   (a) locating a plurality of discriminatory subregions in magnetic resonance spectra of biopsies of tissue having known classifiers of a characteristic,
   (b) cross-validating the spectra by selecting a first portion of the spectra comprising a first plurality of the spectra leaving the remainder of the spectra, developing linear discriminant analysis classifiers from said first portion of spectra, and validating the remainder of the spectra using the classifiers from the first portion of the spectra, to obtain optimized linear discriminant analysis coefficients, (c) repeating step (b) a plurality of times, each time selecting a different portion of the spectra to form the first portion, to obtain a different set of optimized linear discriminant analysis coefficients for each of said plurality of times; and (d) obtaining an average of the linear discriminant analysis coefficients to obtain final classifier spectra indicating the classification of the characteristic based on the spectra, wherein spectra from a biopsy of tissue of unknown classification of a characteristic may be compared to the final classifier spectra to determine the classification of the characteristic of the tissue.

6. An apparatus for obtaining a statistical classifier for classifying spectral data from a biopsy of tissue to determine the classification of a characteristic of the tissue, comprising:

(a) a locator for locating a plurality of discriminatory subregions in magnetic resonance spectra of biopsies of tissue having known classifiers of a characteristic of tissue, (b) a crossvalidator for selecting a first portion of the spectra comprising a first plurality of the spectra leaving the remainder of the spectra, developing linear discriminant analysis classifiers from said first portion of spectra, and validating the remainder of the spectra using the classifiers from the first portion of the spectra to form the first portion, to obtain optimized linear discriminant analysis coefficients, said cross-validator selecting, developing and validating a plurality of times, each time selecting a different portion of the spectra, to obtain a different set of optimized linear discriminant analysis coefficients for each of said plurality of times, and (c) an averager for obtaining an average of the linear discriminant analysis coefficients to obtain final classifier spectra indicating the classification of the characteristic based on the spectra, whereby spectra from a biopsy of tissue of unknown classification of a characteristic may be compared to the final classifier spectra to determine the classification of the characteristic of the tissue.

7. A method for determining the classification of a characteristic of tissue, comprising:

obtaining magnetic resonance spectra of a biopsy of tissue having unknown classification of a characteristic and comparing the spectra with a classifier, said classifier having been obtained by:

(a) locating a plurality of discriminatory subregions in the magnetic resonance spectra of biopsies of tissue having known classifications of a characteristic of the tissue, (b) cross-validating the spectra of (a) by selecting a first portion of spectra comprising a first plurality of the spectra leaving the remainder of the spectra, developing linear discriminant analysis classifier from said first portion of spectra, and validating the remainder of the spectra using the classifications from the first portion of the spectra, to obtain optimized linear discriminant analysis coefficients, (c) repeating step (b) a plurality of times, each time selecting a different portion of the spectra to form the first portion, to obtain a different set of optimized linear discriminant analysis coefficients for each of said plurality of times, and (d) obtaining a weighted average of the linear discriminant analysis coefficients to obtain final classifier spectra indicating the classification of the characteristic based on the spectra, wherein the spectra from the biopsy of tissue having unknown classification may be compared to the final classifier spectra to determine the classification of the characteristic of the tissue.

8. An apparatus for determining the classification of a characteristic of tissue, comprising:

a spectrometer for obtaining magnetic resonance spectra of a biopsy of tissue having unknown classification of a characteristic;

a classifier for statistically classifying the spectra by comparing the spectra with a reference classifications, said classifier having been obtained by:

(a) locating a plurality of discriminatory subregions in the magnetic resonance spectra of biopsies of tissue having known classifications of a characteristic of the tissue, (b) cross-validating the spectra of (a) by selecting a first portion of spectra comprising a first plurality of the spectra leaving the remainder of the spectra, developing linear discriminant analysis classifier from said first portion of spectra, and validating the remainder of the spectra using the classifiers from the first portion of the spectra, to obtain optimized linear discriminant analysis coefficients, (c) repeating step (b) a plurality of times, each time selecting a different portion of the spectra to form the first portion, to obtain a different set of optimized linear discriminant analysis coefficients for each of said plurality of times, and (d) obtaining an average of the linear discriminant analysis coefficients to obtain final classifier spectra indicating the classification of the characteristic based on the spectra, and wherein said classifier compares the spectra from the biopsy of tissue having unknown classification to the final classifier spectra to determine the classification of the characteristic of the tissue.

* * * * *